(12) United States Patent
Caldara (10) Patent No.: US 9,709,445 B2
(45) Date of Patent: Jul. 18, 2017

(54) TEMPERATURE SENSOR AND RELATED METHOD

(71) Applicant: Michele Caldara, Bergamo (IT)

(72) Inventor: Michele Caldara, Bergamo (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 641 days.

(21) Appl. No.: 14/063,464

(22) Filed: Oct. 25, 2013

(65) Prior Publication Data

US 2015/0117494 A1    Apr. 30, 2015

(51) Int. Cl.
| | |
|---|---|
| *G01K 7/01* | (2006.01) |
| *G01K 13/00* | (2006.01) |
| *A61B 5/01* | (2006.01) |
| *A61B 5/00* | (2006.01) |

(52) U.S. Cl.
CPC ............... *G01K 7/01* (2013.01); *A61B 5/01* (2013.01); *G01K 13/002* (2013.01); *A61B 5/0008* (2013.01); *A61B 5/6804* (2013.01)

(58) Field of Classification Search
CPC ..................................................... G01K 7/346
USPC .......................................................... 374/103
See application file for complete search history.

(56) References Cited

U.S. PATENT DOCUMENTS

| | | | | |
|---|---|---|---|---|
| 5,589,688 | A | * 12/1996 | Kimura | ........... H01L 31/035281 |
| | | | | 250/338.4 |
| 6,297,761 | B1 | * 10/2001 | Barrenscheen | ......... H03M 1/50 |
| | | | | 341/118 |
| 6,629,776 | B2 | * 10/2003 | Bell | ........................ G01K 7/245 |
| | | | | 340/539.1 |
| 7,315,461 | B2 | * 1/2008 | Kyono | .................... H02M 1/32 |
| | | | | 323/907 |

(Continued)

FOREIGN PATENT DOCUMENTS

| | | | | |
|---|---|---|---|---|
| JP | 04270492 | A | * | 9/1992 |
| JP | 05040064 | A | * | 2/1993 |

OTHER PUBLICATIONS

Rathore (Digital Measurement Techniques, 2003, Alpha Science International, pp. 35-39).*

(Continued)

*Primary Examiner* — Minh Phan
*Assistant Examiner* — Leon W Rhodes, Jr.
(74) *Attorney, Agent, or Firm* — Seed IP Law Group LLP (57) ABSTRACT

A temperature sensor, including a conduction path, between a line at a supply voltage and a common ground terminal of the temperature sensor, including a capacitor, a resistor and a reverse biased diode a junction temperature of which is to be sensed; a digital circuit coupled with the capacitor, the resistor and the diode, configured to compare a charge voltage of the capacitor with an upper threshold voltage and with a lower threshold voltage, and to generate in operation an output sense signal that switches to a first logic level (Continued)

when the charge voltage attains the lower threshold voltage and to a second logic level when the charge voltage attains the upper threshold voltage, the digital circuit being configured to connect the resistor electrically in parallel with the capacitor to discharge the capacitor when the output sense signal is at the second logic level, and to connect the capacitor so as to be charged by a reverse saturation current flowing throughout the reverse biased diode when the output sense signal is at the first logic level.

16 Claims, 4 Drawing Sheets

(56) References Cited

U.S. PATENT DOCUMENTS

| | | | | |
|---|---|---|---|---|
| 7,619,486 | B1* | 11/2009 | Lesea | H03L 1/022 |
| | | | | 331/176 |
| 9,171,977 | B2* | 10/2015 | Zhang | H01L 31/0312 |
| 2014/0121557 | A1* | 5/2014 | Gannon | A61B 5/002 |
| | | | | 600/549 |
| 2014/0341257 | A1* | 11/2014 | Bernardinis | G01K 7/01 |
| | | | | 374/178 |

OTHER PUBLICATIONS

Bakker, "CMOS Smart Temperature Sensors—An Overview," *Proceedings of IEEE Sensors 2*:1423-1427, 2002.

Caldara et al., "A wearable sensor platform to monitor sweat pH and skin temperature," IEEE International Conference on Body Sensor Networks (BSN), Cambridge, MA, May 6-9, 2013, pp. 1-6.

* cited by examiner

TEMPERATURE SENSOR AND RELATED METHOD

TECHNICAL FIELD

This disclosure relates to temperature sensors and more particularly to a semiconductor temperature sensor, that can implement a related method, adapted to generate a sense signal in digital form representative of a sensed temperature.

BACKGROUND

Temperature sensors are widely used in various fields, such as, for example, in automation, or for medical applications or also in devices installed on wearable supports for continuously monitoring patients.

These so-called smart temperature sensors are widely applied in PCs and laptops to monitor the temperature of the microprocessor, the case, and power-consuming peripheral ICs. This application requires low-cost temperature sensors with a relatively coarse temperature resolution, the analog output of which is converted into a digital signal with an on-chip analog-to-digital converter, that provides the temperature information in digital form to digital blocks of the chip for allowing thermal management of the device.

The article of A. Bakker "CMOS Smart Temperature Sensors—An Overview", *Proceedings of IEEE Sensors*, Vol. 2, pages 1423-1427, 2002, provides a comprehensive overview of CMOS smart temperature sensors. They are substantially based on directly-biased semiconductor PN junctions having two transistors thermally in contact with the element whose temperature is to be sensed. These temperature sensors provide, in ideal conditions, that is when the reverse saturation currents of the two transistors are precisely the same, an analog sense voltage that is directly proportional to the absolute temperature of the junctions.

Unfortunately, process spread causes significant differences between the reverse saturation currents of the transistors, thus the generated analog sense voltage may depend from temperature with a law that greatly differs in an unknown fashion from the expected (proportionality) relation. This source of error can be reduced by using a single transistor twice: two constant currents with a known ratio are generated by an external circuit. However there is still the problem of weak sensitivity (<100 uV/C*log n(ratio of currents)) which creates the need for a low-noise amplification chain that may be expensive. Moreover, the sense voltage should be converted into digital form in order to be provided in input to a microcontroller, thus an analog-to-digital converter is needed, with consequent increase of costs, power consumption, and further worsening of the accuracy of the digital information received by the microcontroller.

For these reasons, temperature sensors based upon PN junctions may be considered intrinsically coarse (typical sensitivity 2-3 mV/° C. with a single transistor used once, <100 uV/C with a single transistor used twice, typical accuracy ±0.1C) and with considerable power consumption and complexity.

In an attempt to devise new temperature sensors with enhanced properties, the present trend of research is pointing towards temperature sensors that do not use PN junctions, such as thermistors or resistance temperature detectors (RTD), that are characterized by refined sensitivity and accuracy.

Unfortunately, accurate RTDs and thermistors are relatively expensive, thus they may not be adequate for providing disposable temperature sensors destined to be installed on wearable supports for monitoring patients. Moreover, they provide a temperature sense signal in analog form, thus an analog-to-digital converter is still required.

SUMMARY

Contrary to what may be commonly assumed in the art, the inventors have found that it is possible to realize very high sensitivity/resolution and low-cost low-power temperature sensors based on semiconductor junctions, that are even capable of generating a temperature sense signal directly in quasi-digital form (PWM, pulse-width-modulated), without using any analog-to-digital converter. Therefore eliminating the need for a complex external constant-current bias, and a low-noise amplification chain followed by expensive and power-hungry analog-to-digital converters. The conversion to the digital domain can instead be performed by using common inexpensive and low-power peripherals such as timers to count clock-ticks of the PWM's duty cycle.

The high-sensitivity and resolution of the embodiments can be used in systems where heat flux is measured by computing the ratio between a temperature difference and a known thermal resistance.

According to an embodiment, there is provided a temperature sensor, comprising a conduction path, between a line at a supply voltage and a common ground terminal of the temperature sensor, including a capacitor, a resistor and a reverse biased diode a junction temperature of which is to be sensed; a digital circuit coupled with said capacitor, said resistor and said diode, configured to compare a charge voltage of said capacitor with an upper threshold voltage and with a lower threshold voltage, and to generate in operation an output sense signal that switches to a first logic level when said charge voltage attains said lower threshold voltage and to a second logic level when said charge voltage attains said upper threshold voltage, said digital circuit being configured to connect said resistor electrically in parallel with said capacitor to discharge said capacitor when said output sense signal is at said second logic level, and to connect said capacitor so as to be charged by a reverse saturation current flowing throughout said reverse biased diode when said output sense signal is at said first logic level.

According to another embodiment, said digital circuit comprises a comparator with hysteresis configured to receive as input the charge voltage of said capacitor, to compare the charge voltage with an upper threshold voltage and with a lower threshold voltage, and to generate in operation an output sense signal that switches to a first logic level when said charge voltage attains said lower threshold voltage, and to a second logic level when said charge voltage attains said upper threshold voltage; and a controlled switch configured to connect said resistor electrically in parallel with said capacitor when said output sense signal is at said second logic level, and to connect said capacitor so as to be charged by a reverse saturation current flowing throughout said reverse biased diode when said output sense signal is at said first logic level.

According to another embodiment, said reverse biased diode is a Schottky diode.

According to another embodiment, the temperature sensor comprises a plurality of reverse biased Schottky diodes connected electrically in parallel among them.

According to another embodiment, said lower threshold voltage is one third of said supply voltage and said upper threshold voltage is two third of said supply voltage.

According to another embodiment, said first logic level is high and said second logic level is low.

According to another embodiment, said digital circuit is a 555 timer IC configured as an astable circuit.

According to an embodiment, there is provided a wearable apparatus for monitoring the health state of a patient, comprising a temperature sensor including a conduction path, between a line at a supply voltage and a common ground terminal of the temperature sensor, including a capacitor, a resistor and a reverse biased diode a junction temperature of which is to be sensed; a digital circuit coupled with said capacitor, said resistor and said diode, configured to compare with hysteresis a charge voltage of said capacitor with an upper threshold voltage and with a lower threshold voltage, and to generate in operation an output sense signal that switches to a first logic level when said charge voltage attains said lower threshold voltage and to a second logic level when said charge voltage attains said upper threshold voltage, said digital circuit being configured to connect said resistor electrically in parallel with said capacitor to discharge said capacitor when said output sense signal is at said second logic level, and to connect said capacitor so as to be charged by a reverse saturation current flowing throughout said reverse biased diode when said output sense signal is at said first logic level, wherein said reverse biased diode is embedded in said apparatus such to be in contact with the skin of the patient when the apparatus is worn.

A method of generating an output sense signal representative of a junction temperature of a reverse biased diode, comprising providing and installing a conduction path, between a line at a supply voltage and a common ground terminal, including a capacitor, a resistor and a reverse biased diode a junction temperature of which is to be sensed; comparing a charge voltage of said capacitor with an upper threshold voltage and with a lower threshold voltage; generating said output sense signal that switches to a first logic level when said charge voltage attains said lower threshold voltage and to a second logic level when said charge voltage attains said upper threshold voltage; connecting said resistor electrically in parallel with said capacitor to discharge said capacitor when said output sense signal is at said second logic level, and connecting said capacitor so as to be charged by a reverse saturation current flowing throughout said reverse biased diode when said output sense signal is at said first logic level.

According to another embodiment, the digital circuit further comprises a hysteresis comparator.

According to another embodiment, the comparing is done using a hysteresis comparator.

The claims as filed are integral part of this specification and are herein incorporated by reference.

DETAILED DESCRIPTION

Figure 1:
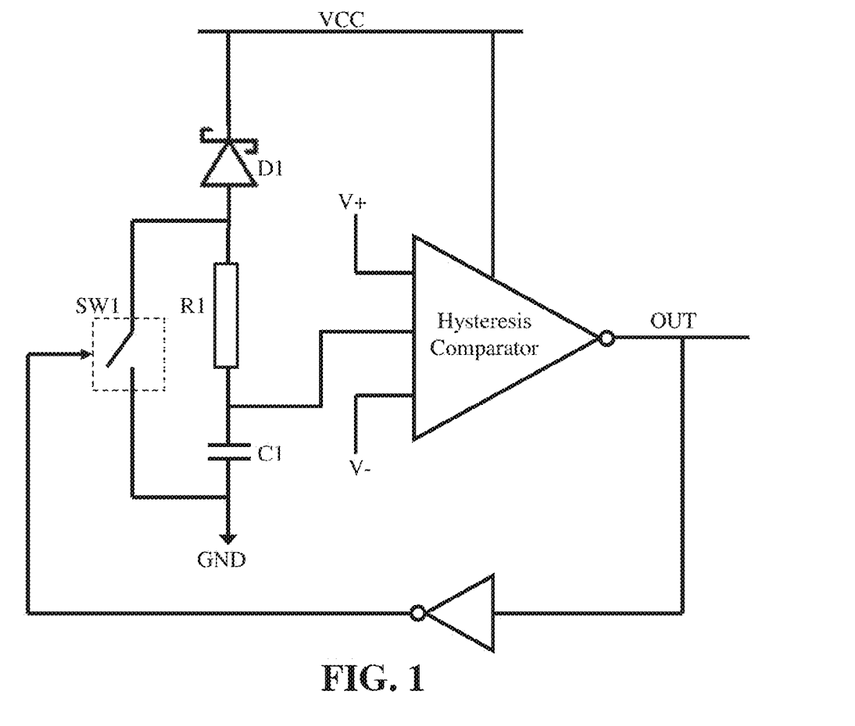
FIG. 1 shows an embodiment of a temperature sensor of this disclosure.

An embodiment of a temperature sensor in accordance with this disclosure is depicted in FIG. 1. The temperature sensor comprises a reverse biased diode D1 as a temperature-sensitive element, connected in series with a resistor R1 and a capacitor C1. The charge voltage of the capacitor C1 is compared by a comparator with hysteresis with an upper threshold V+ and a lower threshold V−, that generates an on/off output voltage OUT that switches to high when the charge voltage attains the lower threshold V− and that switches low when the charge voltage attains the upper threshold V+. The node shared by the diode D1 and the resistor R1 is connected to a line that is alternately set in a high impedance condition (by opening the switch SW1) when the output voltage OUT is high, for charging the capacitor C1 throughout the series connection of the diode D1 and the resistor R1, or grounded when the output voltage OUT is low, to discharge the capacitor C1 through the resistor R1.

With this technique, the output voltage OUT remains logically high (ON level) for a time interval that depends upon the time constant of the exponential charge of the capacitor C1, that is the product between the capacitance C1 and the sum of the resistances of the resistor R1 and of the reverse biased diode D1, and remains logically low (OFF level) for a time interval determined by the time constant of the exponential discharge of the capacitor C1, that is the product between the capacitance C1 and the resistance of the resistor R1. Therefore, the duration of the OFF level of the output voltage OUT is substantially constant with temperature, and the duration of the ON level of the output voltage OUT is a function of the temperature of the semiconductor junction of the diode. By neglecting the dependence of the reverse saturation current from the anode-cathode voltage, the diode D1 may be modeled as a temperature dependent current generator thus in practice the capacitor C1 is charged with the reverse saturation current flowing throughout the diode D1 (that depends upon temperature), and is discharged through the resistor R1, the resistance of which is assumed to be substantially independent from temperature at least in the temperature range of interest. Therefore, the duty-cycle of the output voltage OUT is tied to the value of the reverse saturation current and thus to the temperature of the junction. The output signal also has improved immunity to noise due to the intrinsic low pass filter in the signal formation integrating a charge on capacitor C1.

As an alternative embodiment, the logic values of the output voltage OUT may be inverted: in this case, the switch SW1 is controlled by the output voltage OUT and not by the inverted replica thereof, as in FIG. 1.

The temperature sensor of FIG. 1 does not require an analog-to-digital converter because it generates directly a digital signal OUT that contains information in digital form (the duty-cycle of the output voltage OUT) about the temperature of the junction. Moreover, it operates in reverse biasing conditions, thus temperature fluctuations due to self-heating of the diode during the functioning may be neglected.

The diode D1 in the circuit of FIG. 1 may be of any kind, for example a PN or a PIN or also a Schottky diode, as shown in FIG. 1 by way of example, because the reverse saturation current of all of them depends upon temperature.

It may be particularly convenient to use a Schottky diode instead of a PN or PIN diode. The reverse saturation current density $J_S$ throughout a PN junction depends from temperature with a relatively complicated law, that is typically estimated as follows:

$$J_S = q \cdot n_i^2 \cdot \left( \frac{\sqrt{D_p/\tau_p}}{N_D} + \frac{\sqrt{D_p/\tau_n}}{N_A} \right)$$

wherein
$J_S$ is the reverse saturation current density;
Q is the elementary charge;
$D_{p,n}$ are the diffusion coefficients of holes and electrons, respectively;
$N_{D,A}$ are the donor and acceptor concentrations at the N side and the P side, respectively;
$n_i$ is the intrinsic carrier concentration in the semiconductor material;
$\tau_{p,n}$ are the carrier lifetimes of holes and electrons, respectively.

The intrinsic carrier concentration depends on temperature:

$$n_i^2 = B \cdot T^3 \cdot \exp\left(-\frac{E_{G0}}{kT}\right)$$

wherein
T is the absolute temperature;
$E_{G0}$ is the band gap extrapolated to absolute zero; and
B is a constant that is essentially independent on temperature.

In the range of temperatures of interest (in general from 0° C. up to the maximum operating junction temperature of diode indicated in datasheets, that is typically of about 125° C.), and more particularly in the range of temperatures of the skin of the human body, the diffusion coefficients of holes and electrons may be assumed to be proportional to the absolute temperature T and the carrier lifetimes also depends on temperature, thus the reverse saturation current density $J_S$ of PN junctions depends on temperature with a relatively complex law:

$$J_S = B' \cdot T^\gamma \cdot \exp\left(-\frac{E_{G0}}{kT}\right)$$

wherein B' is a temperature independent constant and γ is an exponent that is to be determined in order to make the above equation describe fairly the real temperature dependence of the reverse saturation current density of PN diodes.

The inventors have found that using a Schottky diode in the circuit of FIG. 1 allows the realization of a very sensitive and high resolution temperature sensor.

Figure 2:
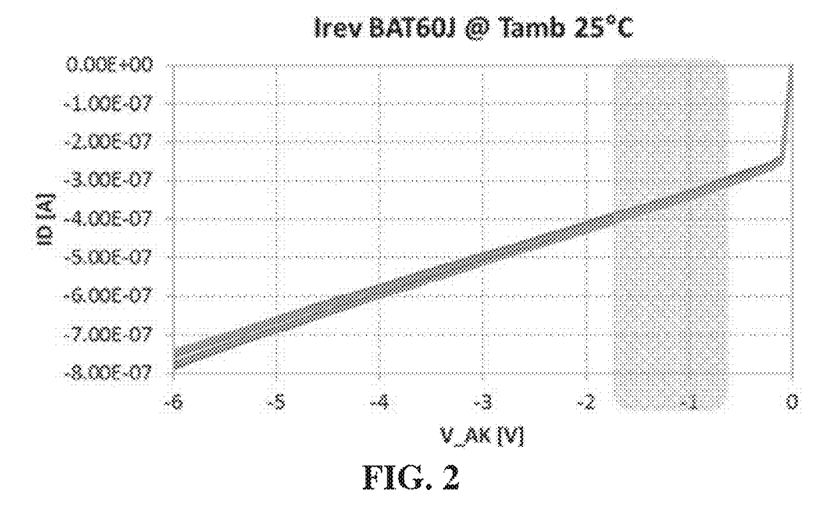
FIG. 2 compares voltage-current characteristics of numerous Schottky diodes of a same production batch.

In general, the reverse saturation current density of Schottky diodes depends on temperature and on other parameters of the diode. The inventors have found that process spreads have little influence on the value of $J_S$, as schematically shown in the current-voltage characteristics $I_D$-$V_{AK}$ depicted in FIG. 2 of Schottky diodes of the type BAT60J belonging to a same production batch, at a temperature of 25° C. Moreover, the inventors have found that the reverse saturation current density is dependent on temperature only according to the following exponential law:

$$J_S \propto \exp\left(-\frac{F}{kT}\right)$$

wherein F is a term independent from temperature and the symbol ∝ means "proportional to". Such an exponential law accurately tracks the real dependence from temperature of the reverse saturation current density in a relatively broad range of temperatures of interest and practically matches it in a temperature range from about 30° C. to about 40° C. Therefore, by using a Schottky diode in the circuit of FIG. 1, it is possible to realize a very sensitive and accurate temperature sensor, to be used in wearable applications for monitoring patients. In order to improve absolute accuracy, the sensor can be calibrated by combining it with conventional methods using a forward biased diode (with single constant current bias and sensitivity ~2 mV/C or double constant current bias and sensitivity of ~100 uV/C).

The advantage of having a very high-sensitivity and resolution temperature sensor for heat-flux measurement where heat flux is measured by computing the ratio between a temperature difference and a known thermal resistance has been described. In this case, absolute accuracy may not be needed.

Figure 3:
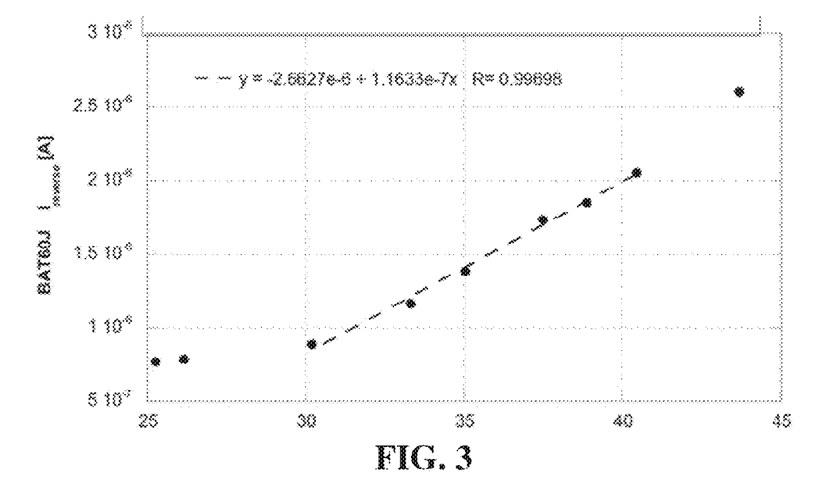
FIG. 3 shows a temperature-current characteristic of a reverse biased Schottky diode at a human skin temperature range.

The inventors have found that the reverse saturation current of Schottky diodes may even be approximated with a straight line in the temperature range from about 30° C. to about 40° C. The graph of FIG. 3, that refers to a Schottky diode of the type BAT60J, shows that increments of the reverse saturation current $I_{reverse}$ from 30° C. up to 41° C. may be calculated using a linear equation with a correlation factor R greater than 0.99, and that it is more than twice greater at 41° C. than at 30° C.

Figure 4:
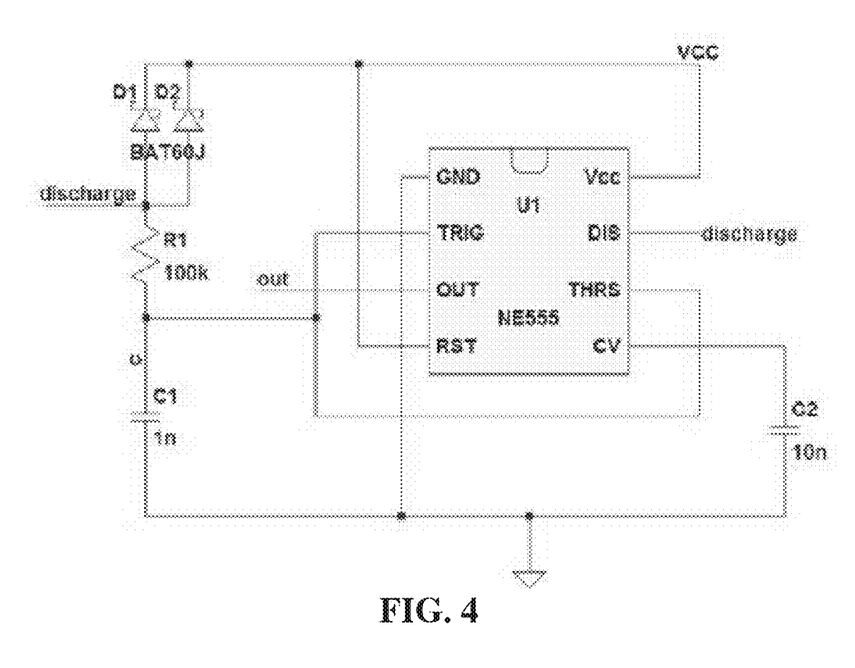
FIG. 4 shows another embodiment of a temperature sensor of this disclosure.

An embodiment of the temperature sensor of this disclosure that uses two (or more) Schottky diodes in parallel is shown in FIG. 4. In this embodiment, there are two Schottky diodes D1 and D2 connected electrically in parallel for increasing the overall reverse saturation current that charges the capacitor C1 and also for averaging effects of process spreads on the dependence of $J_S$ from temperature. The digital circuit composed of the hysteresis comparator and of the controlled switch SW1 shown in FIG. 1 is implemented in FIG. 4 with the chip NE555 manufactured by STMicroelectronics, the datasheet of which is herein incorporated by reference, that is substantially a 555 timer IC configured as an astable circuit. Using the chip NE555, the upper threshold V+ is set equal to VCC*2/3 and the lower threshold V− to VCC/3.

As an alternative, it is possible to use a CMOS 555 timer similar to the chip NE555, such as for example a chip of the type TS555 (TS555C,I,M) manufactured by STMicroelectronics the datasheet of which is herein incorporated by reference, because CMOS 555 timers are characterized by smaller leakage currents than the chip NE555, that is a bipolar timer. Other types of 555 timer ICs may be chosen, provided that they are suitable to operate in the desired range of temperatures.

The values of the capacitors C1 and C2, of the resistor R1 and the identification code of the diodes are merely exemplary and do not limit the invention.

The output voltage OUT may be provided in input to a microcontroller timer peripheral, that extracts the information of temperature from the duty-cycle (or even only from the time duration of the ON level) thereof. With this acquisition method, having a power consumption lower by at least one order of magnitude with respect to using an analog to digital converter (ADC), it is possible to attain a reading resolution better than 0.01° C. For those reasons the temperature sensor is particularly suitable in detecting small temperature gradients.

Figure 5:
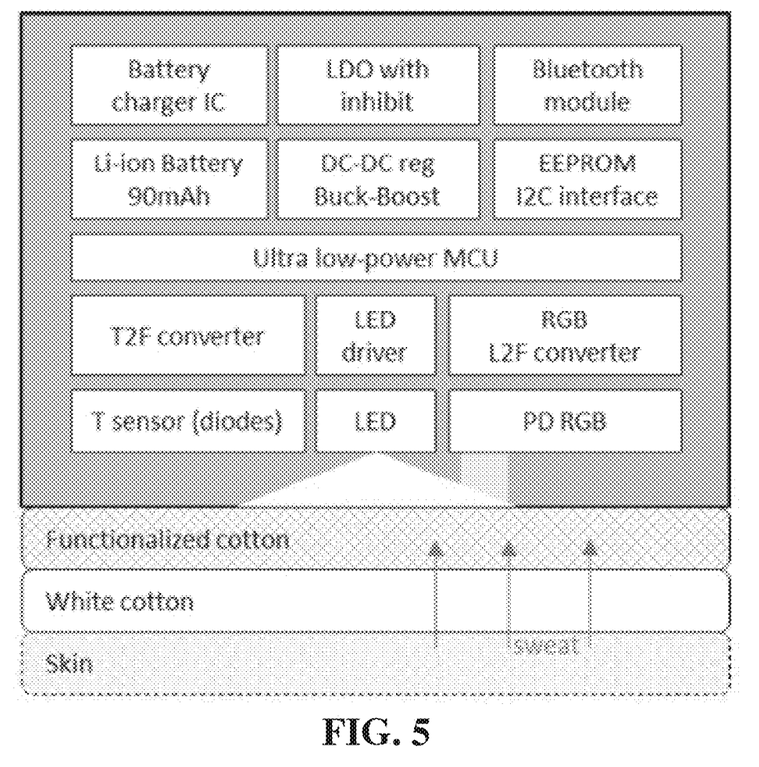
FIG. 5 is a high-level block diagram of a wearable sensing module that includes the temperature sensor of FIG. 4.

The temperature sensor of this disclosure may be embedded in a wearable sensing system such as the one shown in FIG. 5 and disclosed in the paper of M. Caldara et al. "A wearable sensor platform to monitor sweat pH and skin temperature", *IEEE International Conference on Body Sensor Networks* (*BSN*), 6-9 May 2013, pages 1-6, the disclosure of which is herein incorporated by reference, for realizing a wearable apparatus with a low cost though very sensitive and high resolution temperature sensor. The system, as depicted in FIG. 5, is composed of a functionalized textile, which is in contact with the skin, and is capable of changing color depending on the pH of the absorbed sweat, and by miniaturized electronics coupled to the textile, having external dimensions of only 50 mm×47 mm×15 mm. The electronic system includes an RGB color sensor, the temperature sensor, a low-power microcontroller, a non-volatile memory, a Bluetooth V3.0 miniaturized module (Amped'Up BT33) and different blocks dedicated to the power supply and battery management. The system automatically performs sweat and skin temperature measurements, that periodically are transmitted in a wireless fashion to an external device.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A temperature sensor, comprising:
   a conduction path between a line at a supply voltage and a common ground terminal of the temperature sensor and including a series connected capacitor, resistor and a plurality of reverse biased diodes coupled in parallel and being physically proximate each other, a junction temperature of the plurality of reverse biased diodes being sensed; and
   a digital circuit coupled with said capacitor, said resistor and said plurality of reverse biased diodes, the digital circuit configured to compare a charge voltage of said capacitor with an upper threshold voltage and with a lower threshold voltage, and to generate in operation an output sense signal that switches to a first logic level when said charge voltage attains said lower threshold voltage and to a second logic level when said charge voltage attains said upper threshold voltage, said digital circuit being configured to connect said resistor electrically in parallel with said capacitor to discharge said capacitor when said output sense signal is at said second logic level, and to connect said capacitor so as to be charged by reverse saturation currents flowing through said plurality of reverse biased diodes when said output sense signal is at said first logic level.

2. The temperature sensor of claim 1, wherein said digital circuit comprises:
   a comparator with hysteresis configured to receive as input the charge voltage of said capacitor, to compare the charge voltage with an upper threshold voltage and with a lower threshold voltage, and to generate in operation an output sense signal that switches to a first logic level when said charge voltage attains said lower threshold voltage, and to a second logic level when said charge voltage attains said upper threshold voltage; and
   a controlled switch configured to connect said resistor electrically in parallel with said capacitor when said output sense signal is at said second logic level, and to connect said capacitor so as to be charged by a reverse saturation current flowing throughout said reverse biased diode when said output sense signal is at said first logic level.

3. The temperature sensor of claim 1, wherein said reverse biased diode is a Schottky diode.

4. The temperature sensor of claim 1, wherein said lower threshold voltage is one third of said supply voltage and said upper threshold voltage is two thirds of said supply voltage.

5. The temperature sensor of claim 1, wherein said first logic level is high and said second logic level is low.

6. The temperature sensor of claim 1, wherein said digital circuit is a 555 timer IC configured as an astable circuit.

7. The temperature sensor of claim 1, wherein the digital circuit further comprises a hysteresis comparator.

8. The temperature sensor of claim 1, further comprising a timer circuit configured to convert temperature information to a digital signal.

9. A wearable apparatus for monitoring the health state of a patient, comprising:
   a temperature sensor including a conduction path between a line at a supply voltage and a common ground terminal of the temperature sensor, the conduction path including a capacitor, a resistor and a plurality of parallel-connected reverse biased diodes, connected in series between the line at the supply voltage and the common ground terminal, wherein a reverse saturation current through each of the plurality of parallel-connected reverse biased diodes is function of a junction temperature of the diode and wherein each of the plurality of parallel-connected reverse biased diodes is positioned relative to the other ones of the plurality of parallel-connected reverse biased diodes so the junction temperatures of all the plurality of parallel-connected reverse biased diodes are approximately equal;
   a digital circuit coupled with said capacitor, said resistor and said plurality of parallel-connected reverse biased diodes, the digital circuit configured to compare a charge voltage of said capacitor with an upper threshold voltage and with a lower threshold voltage, and to generate an output sense signal that switches to a first logic level when said charge voltage attains said lower threshold voltage and to a second logic level when said charge voltage attains said upper threshold voltage, said digital circuit being configured to connect said resistor electrically in parallel with said capacitor so that substantially no reverse saturation currents flowing through said plurality of parallel-connected reverse biased diodes flows to said capacitor, and configured to discharge said capacitor through the resistor when said output sense signal is at said second logic level and to connect said capacitor so as to be charged by the reverse saturation current flowing throughout said reverse biased diode when said output sense signal is at said first logic level,
   wherein said reverse biased diode is embedded in said apparatus such to be in contact with the skin of the patient when the apparatus is worn.

10. The wearable apparatus of claim 9, wherein the digital circuit further comprises a hysteresis comparator.

11. The wearable apparatus of claim 9, further comprising a timer circuit configured to convert temperature information to a digital signal.

12. A method of generating an output sense signal representative of a junction temperature of a reverse biased diode, comprising:

providing a plurality of reverse biased diodes coupled in parallel and positioned proximate one another to approximately equalize junction temperatures of the plurality of reverse biased diodes;

providing a conduction path between a line at a supply voltage and a common ground terminal, the conduction path including the plurality of reverse biased, a capacitor, and a resistor, coupled in series in that order between the line at the supply voltage and the common ground terminal;

comparing a charge voltage of said capacitor with an upper threshold voltage and with a lower threshold voltage;

generating said output sense signal that switches to a first logic level responsive to said charge voltage attaining said lower threshold voltage and to a second logic level responsive to said charge voltage attaining said upper threshold voltage;

coupling said resistor electrically in parallel with said capacitor by coupling a node defined at the interconnection of the plurality of reverse biased diodes and the resistor to the common ground terminal to discharge said capacitor when said output sense signal is at said second logic level, and coupling said capacitor so as to be charged by total reverse saturation current equal to the sum of respective reverse saturation currents flowing through the plurality of reverse biased diodes when said output sense signal is at said first logic level by isolating the node defined at the interconnection of the reverse biased diode and the resistor from the common ground terminal.

13. The method of claim 12, wherein the comparing is done using a hysteresis comparator.

14. The method of claim 12, further comprising converting temperature information to a digital signal using a timer circuit.

15. The method of claim 12, wherein coupling the node defined at the interconnection of the reverse biased diode and the resistor to the common ground terminal comprises closing a switch coupled between the node and the common ground terminal.

16. The method of claim 15, wherein isolating the node defined at the interconnection of the reverse biased diode and the resistor from the common ground terminal comprises opening the switch.

* * * * *